(12) United States Patent
Dibb et al.

(10) Patent No.: US 7,928,282 B2
(45) Date of Patent: Apr. 19, 2011

(54) ABSORBENT PRODUCTS WITH A LINKED ENZYME TREATMENT

(75) Inventors: Karyn Clare Dibb, Neenah, WI (US); David Charles Potts, Dunwoody, GA (US); Jack Nelson Lindon, Alpharetta, GA (US); Alice Y. Romans-Hess, Pinehurst, NC (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1362 days.

(21) Appl. No.: 10/837,133

(22) Filed: Apr. 30, 2004

(65) Prior Publication Data
US 2005/0256471 A1 Nov. 17, 2005

(51) Int. Cl.
*A61F 13/15* (2006.01)
*A61F 13/20* (2006.01)
*C04B 9/02* (2006.01)
*B32B 5/12* (2006.01)
*B32B 27/04* (2006.01)

(52) U.S. Cl. ........... 604/367; 604/378; 106/14.15; 442/58; 442/93; 442/152; 442/158

(58) Field of Classification Search .......... 604/367, 604/385.01, 359–360, 368; 435/267–269, 435/263
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,585,998 A * | 6/1971 | Hayford et al. | 604/359 |
| 3,616,229 A | 10/1971 | Wildi et al. | |
| 3,625,827 A * | 12/1971 | Wildi et al. | 435/175 |
| 3,692,618 A | 9/1972 | Dorschner et al. | |
| 3,751,561 A | 8/1973 | Wildi et al. | |
| 3,802,817 A | 4/1974 | Matsuki et al. | |
| 3,849,241 A | 11/1974 | Butin et al. | |
| 3,855,046 A | 12/1974 | Hansen et al. | |
| 4,006,059 A | 2/1977 | Butler | |
| 4,102,746 A * | 7/1978 | Goldberg | 435/96 |

(Continued)

FOREIGN PATENT DOCUMENTS
EP 0476574 B1 5/2001
(Continued)

OTHER PUBLICATIONS
Machine English translation of JP 06-090978.*
(Continued)

*Primary Examiner* — Melanie J Hand
(74) *Attorney, Agent, or Firm* — Ralph H. Dean, Jr.; David J. Arteman

(57) ABSTRACT

The present invention provides a substrate treated with an linked enzyme. It has been discovered that a substrate treated with a linked enzyme can be effective in improving the ability of the substrate to absorb viscoelastic materials, such as menses, by cleaving a protein structure present in some viscoelastic materials. In addition, the linked enzyme is less likely to migrate from the treated material onto the user, as compare to an enzyme being placed directly on the substrate, thereby reducing the risk of sensitization to the user of the absorbent product. Also provided by the present invention are absorbent articles which contain at least one surface or layer containing the linked enzyme.

38 Claims, 2 Drawing Sheets

U.S. PATENT DOCUMENTS

| | | | |
|---|---|---|---|
| 4,340,563 A | | 7/1982 | Appel et al. |
| 4,488,928 A | | 12/1984 | Ali Khan et al. |
| 4,690,680 A | * | 9/1987 | Higgins ................ 604/386 |
| 4,973,469 A | * | 11/1990 | Mulligan et al. ............ 424/461 |
| 5,108,820 A | | 4/1992 | Kaneko et al. |
| 5,108,827 A | | 4/1992 | Gessner |
| 5,336,552 A | | 8/1994 | Strack et al. |
| 5,382,400 A | | 1/1995 | Pike et al. |
| 5,441,740 A | | 8/1995 | Ozlen |
| 5,460,832 A | | 10/1995 | Yamaguchi et al. |
| 5,762,642 A | * | 6/1998 | Coles et al. ............... 604/378 |
| 5,869,172 A | | 2/1999 | Caldwell |
| 5,958,758 A | * | 9/1999 | Miller et al. ................ 435/268 |
| 6,028,016 A | | 2/2000 | Yahiaoui et al. |
| 6,045,900 A | | 4/2000 | Haffner et al. |
| 6,060,636 A | | 5/2000 | Yahiaoui et al. |
| 6,066,494 A | | 5/2000 | Hsieh et al. |
| 6,116,780 A | * | 9/2000 | Young et al. ................ 383/44 |
| 6,350,711 B1 | * | 2/2002 | Potts et al. ................ 442/123 |
| 6,355,583 B1 | | 3/2002 | Yahiaoui et al. |
| 6,416,769 B1 | | 7/2002 | Vromen |
| 6,417,154 B1 | | 7/2002 | Yahiaoui et al. |
| 6,610,898 B1 | * | 8/2003 | Magnusson et al. ......... 604/366 |
| 6,639,119 B2 | * | 10/2003 | Roe et al. ..................... 604/367 |
| 6,649,099 B2 | | 11/2003 | Potts et al. |
| 6,649,805 B1 | * | 11/2003 | Carlucci et al. ............. 604/359 |
| 6,673,982 B1 | | 1/2004 | Chen et al. |
| 6,713,660 B1 | | 3/2004 | Roe et al. |
| 6,737,079 B2 | * | 5/2004 | Fischetti et al. ............. 424/447 |
| 2001/0044614 A1 | | 11/2001 | Damay et al. |
| 2001/0053902 A1 | * | 12/2001 | Roe et al. ................. 604/385.01 |
| 2002/0040210 A1 | | 4/2002 | Luccio et al. |
| 2002/0065495 A1 | | 5/2002 | Potts et al. |
| 2003/0077307 A1 | | 4/2003 | Klofta et al. |
| 2003/0124936 A1 | | 7/2003 | Potts et al. |
| 2003/0135172 A1 | * | 7/2003 | Whitmore et al. ........... 604/359 |
| 2003/0139711 A1 | | 7/2003 | Roe et al. |
| 2003/0208173 A1 | * | 11/2003 | Lagerstedt-Eidrup et al. ................................. 604/367 |

FOREIGN PATENT DOCUMENTS

| | | | |
|---|---|---|---|
| EP | 1061963 B1 | | 5/2003 |
| GB | 2 147 206 A | | 5/1985 |
| JP | 06090978 | * | 4/1994 |
| JP | 06090978 A | * | 4/1994 |
| JP | 2002058702 | * | 2/2002 |
| KR | 9302270 B | * | 3/1993 |
| KR | 9300002270 A | * | 3/1993 |
| WO | WO 9203172 A1 | * | 3/1992 |
| WO | WO 00/74740 A1 | | 12/2000 |
| WO | WO 0112241 A1 | * | 2/2001 |
| WO | WO 03/002163 | | 1/2003 |
| WO | WO 2004/112851 A1 | | 12/2004 |
| WO | WO 2004112851 A1 | * | 12/2004 |

OTHER PUBLICATIONS

Machine English translation of Ouchi reference, JP 06-090978.*

Fried, Joel R., "Thermoplastics," *Polymer Science and Technology*, Prentice Hall PTR, 1995, p. 299.

"Linked-Papain C-MPB: An Enzyme Alternative to AHA's," Collaborative Laboratories, Internet web page "http://www.collabo.com/linkpap.htm", updated Mar. 4, 2004, viewed and printed Mar. 18, 2004, pp. 1-6.

Manson, John A. and Leslie H. Sperling, "Bicomponent and Biconstituent Fibers," *Polymer Blends and Composites*, Plenum Press, New York, Section 9.2, 1976, pp. 273-277.

* cited by examiner

ABSORBENT PRODUCTS WITH A LINKED ENZYME TREATMENT

FIELD OF THE INVENTION

The present invention relates to a treated substrate and absorbent articles containing the treated substrate. More particularly, the present invention relates to an absorbent article, such as a personal care absorbent article, having viscous fluid handling properties.

BACKGROUND OF THE INVENTION

Absorbent materials and absorbent articles are known in the art and are known to have a wide variety of uses. Examples of such absorbent materials and absorbent articles include, for example, personal care products, such as disposable diapers and training pants; feminine hygiene products, such as sanitary napkins and tampons; incontinent care products, such as pads and undergarments; health care items such as, for example, bandages. Other absorbent materials and absorbent articles include wipers, absorbent mats and soakers. Because the fluids these products are designed to absorb have different properties, it is often difficult to provide an absorbent material which will efficiently absorb a wide variety of fluids. Therefore, various treatments for improving the absorbency, fluid distribution and fluid retention of absorbent materials and absorbent articles have been developed.

Highly viscous fluids are often difficult to absorb into absorbent products. For example, in feminine hygiene products, the viscoelastic properties of menses often make it challenging to absorb and distribute within the feminine hygiene products. The viscosity and/or elastic components of such fluids tend to impose requirements for absorption and/or distribution within the absorbent structure of the absorbent product. These requirements are often inconsistent with the best performance with respect to other components of the fluid that are less viscous or elastic with the result that a compromise in overall performance usually is required. For example, the pore and capillary sizes in an ideal material for absorbing and distributing less viscoelastic components are different from those that work best for the more viscoelastic components. Menses is a viscoelastic fluid composed of blood (primarily red blood cells and plasma), cervical mucus and/or tissue fragments. Mucin is found in virtually all menses samples. Mucin is a large linear glycoprotein having molecular weights up to 20 million or more. In combination with water and salts, mucin is a principal component of mucus, including cervical mucus. Mucin, with its large linear molecules, is believed to form networks in solution, giving rise to viscoelastic properties.

Mucin causes many challenges in menses absorbent products. Mucin in menses reduces intake of the menses fluid through the cover or body facing surface of an absorbent product. In addition, mucin tends to hamper fluid distribution in the absorbent article due to its highly viscoelastic and stringy nature. It is believed that mucin forms a three-dimensional network on the surface of the absorbent product, thereby blocking the intake ability of the absorbent product. When additional insults of menses come into contact with the three-dimensional network on the surface of the absorbent product, the additional insults may flow over the three-dimensional network, thereby causing the absorbent product to leak. Further, if the mucin component does penetrate the surface of the absorbent product, the mucin may clog the pores of the underlying absorbent layers, thereby causing a local saturation (most, if not all, of the pores in an area being filled to capacity) of the absorbent layer and/or the intake layer. The local saturation could cause leakage or prevent further distribution of the menses within the absorbent article or individual layers which may be present in an absorbent article in the x, y and z directions.

In addition to menses, there are other viscous materials which are difficult to absorb, including, for example, feces (or bowel movements), exudates from wounds, mucus, fluids containing food and plant proteins. It has been suggested in the art, as described in U.S. Pat. No. 6,060,636 to Yahiaoui et al. which is hereby incorporated by reference, to use viscoelastant agents such as alkyl polyglycosides having 8-10 carbon atoms in the alkyl chain to reduce the viscosity of viscous fluids. Other viscoelastant agents suggested by Yahiaoui et al. include bovine lipid extract surfactant (Survanta, Ross Laboratories), a drug used to treat Acute Respiratory Distress Syndrome and Cystic Fibrosis, and enzymes such as papain or pepsin, which cleave protein structures. Some dextrans may also be used as viscoelastants. Dextrans are ($\alpha$-1-6) polymers of glucose with chain-like structures and molecular weights up to, for example, 2,000,000 daltons produced from sucrose, often by bacterial action.

Enzymes are known in the art to break-up or cleave proteins such as those found in mucin. However, enzymes can cause skin sensitization. Therefore, placing enzymes directly on an absorbent article may make the absorbent article unusable for some potential users, due to the sensitization the enzymes may cause. Further, the enzymes may migrate from the absorbent article onto the user, such as onto the user's skin. Hence, the use of enzymes in absorbent materials and absorbent articles have been avoided.

There is a need in the art for an absorbent system which will effectively absorb and retain viscous materials, which can use the advantages of enzymes with a reduced risk of sensitization to the user on the absorbent product.

BRIEF DESCRIPTION OF THE INVENTION

Generally stated, the present invention provides a substrate treated with a linked enzyme. It has been discovered that a substrate treated with a linked enzyme can be effective in improving the ability of the substrate to absorb viscoelastic materials, by cleaving a protein structure present in some viscoelastic materials. The use of a linked enzyme, compared to a non-modified enzyme, may reduce sensitization to the skin or mucous membranes if the linked enzyme migrates to the user's body. In addition, the linked enzyme is less likely to migrate from the treated material onto the user, thereby reducing the risk of sensitization to the user of the absorbent product containing the linked enzyme.

More particularly, the present invention provides a treated substrate adapted for use with viscoelastic fluids and having the property of altering the characteristics such as viscosity and/or elasticity of a viscoelastic insult liquid so as to control fluid movement such as intake, distribution, and absorption, of the liquid in personal care product applications such as sanitary napkins.

The present invention also provides an absorbent article containing at least one linked enzyme. More particularly, the absorbent article has a baffle, an absorbent layer and a body side liner, wherein the absorbent layer is positioned between the baffle and the body side liner, wherein at least one of the absorbent layer or the body side liner has the linked enzyme applied thereto. As an alternative configuration, an absorbent article is provided by the present invention wherein the absorbent article has a baffle, an absorbent layer, an intake layer and a body side liner, wherein the absorbent layer is positioned between the baffle and the intake layer, and the intake layer is positioned between absorbent layer and the body side liner, wherein at least one of the absorbent layer, the intake layer or the body side liner has the linked enzyme applied thereto.

The present invention also provides a method of increasing the absorbency of a viscoelastic fluid containing a proteinaceous component into a substrate by providing the substrate with a treatment containing a linked enzyme, wherein the enzyme is a protease.

In each of the aspects of the present invention, the enzyme may be linked to a water soluble polymer, such that the resulting linked enzyme may be placed into an aqueous solution. Any enzyme may be used, but the enzyme should be selected based on the types of components present in the fluids to be absorbed. For example, in the case of proteinaceous components present in bodily exudes such as menses, it is generally desired that the enzyme is a protease. In the case of carbohydrate containing components, it is generally desired that the enzyme is a glycosidase. In the case of mucin, both proteases and glycosidases are effective.

DEFINITIONS

Figure 1:
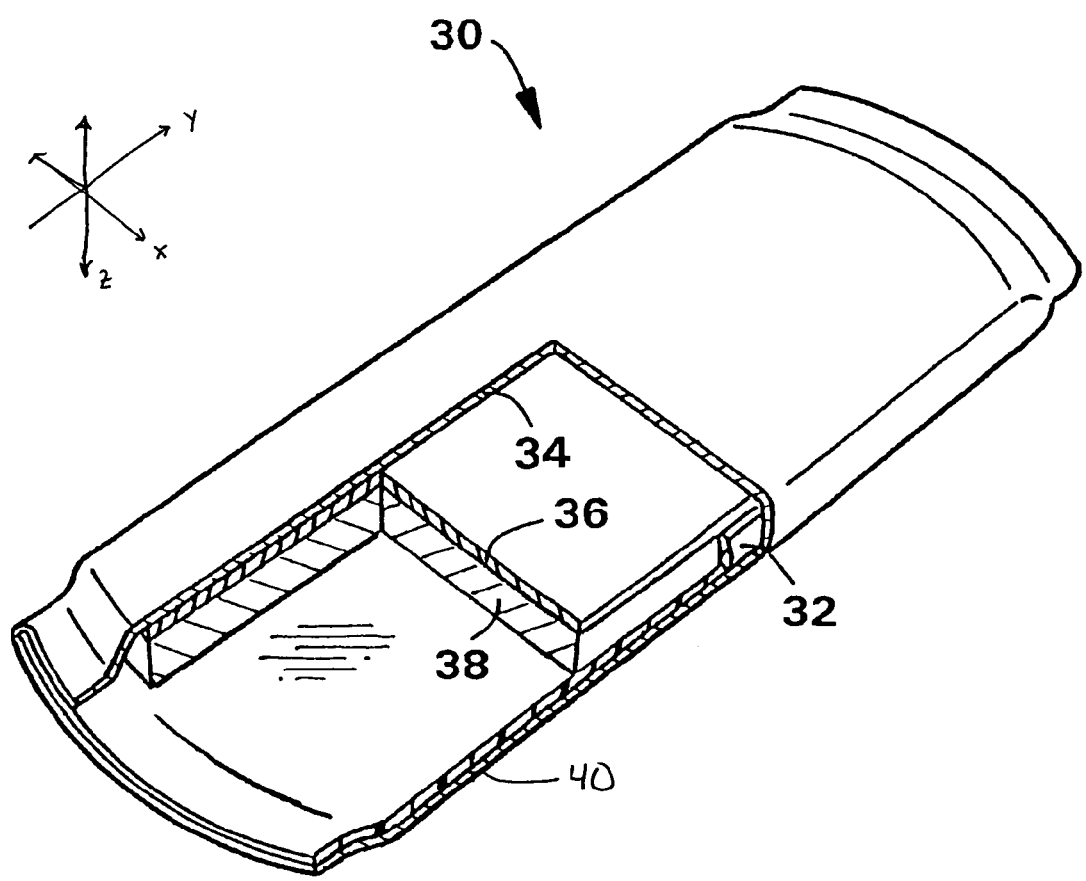
FIG. 1 shows a cut-away view of a typical structure present in a personal care absorbent article.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "viscoelastic" means a composition having at least one significant component that is moderately viscous and/or has elastic properties. By "moderately viscous" it is meant that the component has a viscosity of at least that of normal human blood plasma. By "elastic" it is meant that the component has elasticity equal to or greater than normal human blood.

As used herein, the term "viscoelastant" means an organic agent that, when an effective amount is contacted by a viscoelastic composition, materially alters the properties of that viscoelastic composition, for example, by reducing its viscosity and/or elastic nature. By "materially alters" it is meant that the property measured as described is changed by at least a statistically significant amount and, advantageously, this change will be at least about 30% for many applications.

As used herein, the term "linked enzyme" means an enzyme which is chemically bonded by covalent or ionic bonding to a carrier material which is soluble or dispersible in a solution. This term is also intended to cover a mixture of two or more enzymes chemically bonded to a carrier material.

As used herein, the term "intake" refers to the ability of an absorbent article to absorb fluid. Intake time is used to assess the quality of absorption with lower intake times denoting materials capable of rapid absorption and higher intake times denoting materials with poorer absorption.

As used herein, the term "stain" refers to fluid, wet or dried, which is present on the top surface, in, or on the bottom surface of a cover material, topsheet or body contacting layer of a personal care absorbent article. A "stain" is generally visible to the user of the personal care absorbent article.

As used herein, the term "nonwoven fabric or web" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, airlaying processes and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Levy, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

As used herein, the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly dispersed meltblown fibers. Such a process is disclosed, for example, in U.S. Pat. No. 3,849,241 to Butin. Meltblown fibers are microfibers which may be continuous or discontinuous and are generally smaller than 10 microns in average diameter.

As used herein, "bonded carded webs" or "BCW" refers to nonwoven webs formed by carding processes as are known to those skilled in the art and further described, for example, in coassigned U.S. Pat. No. 4,488,928 to Alikhan and Schmidt which is incorporated herein in its entirety by reference. Briefly, carding processes involve starting with a blend of, for example, staple fibers with bonding fibers or other bonding components in a bulky batt that is combed or otherwise treated to provide a generally uniform basis weight. This web is heated or otherwise treated to activate the adhesive component resulting in an integrated, usually lofty nonwoven material.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein, the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives, e.g. titanium dioxide for color, are generally present in an amount less than 5 weight percent and more typically about 2 weight percent.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement or an "islands-in-the-sea" arrangement. Conjugate fibers are taught in U.S. Pat. No. 5,108,820 to Kaneko et al., U.S. Pat. No. 5,336,552 to Strack et al.; and U.S. Pat. No. 5,382,400 to Pike et al. For two component fibers, the polymers may be present in ratios of 75/25, 50/50, 25/75 or any other desired ratios.

As used herein, the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook Polymer Blends and Composites by John A. Manson and Leslie H. Sperling, copyright 1976 by Plenum Press, a division of Plenum Publishing Corporation of New York, IBSN 0-306-30831-2, at pages 273 through 277.

As used herein, the term "blend" as applied to polymers, means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, through air bonding or "TAB" means a process of bonding a nonwoven, for example, a bicomponent fiber web in which air which is sufficiently hot to melt one of the polymers of which the fibers of the web are made is forced through the web. The air velocity is often between 100 and 500 feet per minute and the dwell time may be as long as 6 seconds. The melting and resolidification of the polymer provide the bonding. Through air bonding has restricted variability and is often regarded a second step bonding process. Since TAB requires the melting of at least one component to accomplish bonding, it is restricted to webs with two components such as bicomponent fiber webs or webs containing an adhesive fiber, powder or the like. TAB is frequently used to bond BCW materials.

As used herein, "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H &P" pattern with about a 30% bond area with about 200 bonds/square inch as taught in U.S. Pat. No. 3,855,046 to Hansen and Pennings. The H &P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g. like a window screen. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

As used herein, the term "layer" means a separate material which is placed next to, bonded or otherwise attached to an adjacent material. Adjacent layers may be prepared for the same material or for different materials.

As used herein, the phrase "absorbent article" refers to devices which absorb and contain liquids. "Personal care absorbent article" or "personal care product" refers to absorbent articles or devices which are placed against or near the skin to absorb and contain the various liquids discharged from the body. Examples of personal care products include, for example diapers, training pants, absorbent underpants, adult incontinence products, sanitary wipes and feminine hygiene products such as sanitary napkins and tampons. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; as well as absorbent wipes and covering mats.

DETAILED DESCRIPTION OF THE INVENTION

It has been discovered that treating a substrate with a linked enzyme can improve the ability of the substrate to intake, distribute or retain a viscoelastic fluid. The linked enzyme helps reduce the viscosity of the viscoelastic fluid by cleaving the viscoelastic components of the fluid into smaller molecules.

Suitable substrates which can be treated with the linked enzyme include films, woven webs, knitted webs, foams or nonwoven webs. These substrates can be prepared by any known method and can be prepared from natural or synthetic materials. Synthetic substrates are generally prepared from a polymeric material. Polymers suitable for preparing the substrate to be treated include polyolefins, polyesters, polyamides, polycarbonates, polyurethanes, polyvinylchloride, polytetrafluoroethylene, polystyrene, polyethylene terephathalate, biodegradable polymers such as polylactic acid and copolymers and blends thereof. Suitable polyolefins include polyethylene, e.g., high density polyethylene, medium density polyethylene, low density polyethylene and linear low density polyethylene; polypropylene, e.g., isotactic polypropylene, syndiotactic polypropylene, blends of isotactic polypropylene and atactic polypropylene, and blends thereof; polybutylene, e.g., poly(1-butene) and poly(2-butene); polypentene, e.g., poly(1-pentene) and poly(2-pentene); poly(3-methyl-1-pentene); poly(4-methyl 1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, and the like, as well as blends and copolymers thereof. Suitable polyesters include polyethylene terephthalate, polytrimethylene terephthalate, polybutylene terephthalate, polytetramethylene terephthalate, polycyclohexylene-1,4-dimethylene terephthalate, and isophthalate copolymers thereof, as well as blends thereof. In addition to polymeric substrates, the substrates of the present invention may be prepared from natural occurring materials, such as woody or non-woody pulp, cotton, rayon, recycled paper, pulp fluff, inorganic absorbent materials, treated polymeric staple fibers and so forth. Desirably, although not required, the absorbent material contains a cellulosic material such as pulp.

Desirably, however, the substrate to be treated with the linked enzyme is a fibrous material such a nonwoven web, from a standpoint of cost. In a further aspect of the present invention, the nonwoven web suitably contains polyolefin fibers and even more suitably polypropylene fibers. Nonwoven fabrics or webs can be formed by many processes such as, for example, meltblowing, spunbonding, coforming, hydroentangling, air-laid and bonded carded web processes and so forth. In the case of air-laid fibers, the fibers can be prepared from other components such as polyesters. These formation processes are described above and are known in the art. The fibers of the nonwoven webs may be monocomponent fibers, multicomponent fibers, multiconstituent fibers or mixtures thereof. Further, blends of these types of fibers with cellulosic fibers, such as pulp, may also be used.

In addition to these substrates, the linked enzyme may be treated onto laminates of two or more of the substrates described above. For example, laminates of two of more nonwoven material can be prepared, such a spunbond/meltblown laminate or a spunbond/meltblown/spunbond laminate, laminate of nonwovens to films, such as a spunbond/film laminate, air-laid/spunbond laminate and the like.

The enzyme can be any type of enzyme. The enzyme is selected based on its ability to modify the viscosity the components present in viscoelastic material to be absorbed into the treated substrate. For example, if the viscoelastic material is a protein based fluid, the enzyme could be a protease. Likewise, if the viscoelastic fluids are carbohydrates, the enzyme could be a glycosidase. In the present invention, it is desirable that the enzyme is a protease since most viscoelastic bodily fluids contain proteins. Suitably, the protease is papain, bromelain, pepsin, trypsin, chymotrypsin, serine proteases or mixtures thereof. Exemplary glycosidases include, for example, an α-amylase, neuraminidase, α- or β-glucosidase, galactosidase, glycosynltransferases and the like. Also mixtures of glycosidases and proteases may be used when the viscoelastic fluid has both protein and carbohydrate, or either the protease or glycosidase may be used. For example, if the viscoelastic fluid is a fluid such as mucus, which is mucin and water, the enzyme could be a protease, a glycosidase or mixtures thereof.

The enzyme is linked to a carrier material. Generally, it is desirable that the enzyme is linked or chemically bonded by covalent or ionic bonding to a carrier material. Ideally, the carrier material is a material which is soluble or dispersible in a solution, in particular, aqueous solutions. The carrier material can be a polymer, or a compound which is dispersible or soluble in solutions. In addition, the carrier can be a material which can be formed into micelles. More desirably, the polymer is soluble or dispersible in an aqueous solution. Desirable, the carrier substrate is soluble in a liquid, and more desirably, the carrier material should be soluble in water. Polymers useable in the present invention as the carrier material include, for example, polyacrylic acid, polyvinylpyrrolidone, polyalkylene oxide, such as polyethylene glycol, polyvinyl alcohol, maleic anhydride polymers and copolymers such as acrylamide-maleic acid hydrogels or ethylene maleic anhydride copolymer and block, graft or random copolymers thereof. Other soluble polymers may also be used. One or more enzymes may be linked to a given carrier material or one or more carrier materials may be used for a given enzyme. For example, the carrier may be a polymer mixture. In addition, the linked enzyme may be a blend of two or more linked enzymes, each having the same or different carrier materials.

Linking of the enzyme can be carried out by techniques known to those skilled in the art. Such techniques are described in U.S. Pat. No. 3,625,827 to Wildi et al. and U.S. Pat. No. 3,616,229 to Wildi et al., both of which are hereby incorporated by reference in their entirety. Generally described, the enzyme or mixture of enzymes are reacted with a polymer in a solution. Desirably, the enzyme is reacted through a group on the enzyme which does not affect the activity of the enzyme once linked to the carrier material. Exemplary reactive groups which generally do not affect the enzymatic activity usually present on enzymes include, for example, amino, hydroxyl, carboxyl, anhydride, mercapto and imidazolyl groups. These groups can be reacted polymers which are adapted to react or couple with the enzyme. Effective reactive groups on the polymers include, for example, carboxyl groups, anhydride groups, amino groups, hydroxyl groups, mercapto groups and the like. The reaction can result in bonding between the enzyme and the polymer which may be ionic or covalent bonding. In some situations, which will be apparent to those skilled in the art, it may be necessary to protect the active groups of the enzyme which give the enzyme its activity from reaction with the reactive groups of the polymer. In such cases, the protecting group must be readily removable from the enzyme and such protecting techniques are readily apparent to those skilled in the art. Other possible methods of linking enzymes to carriers could include reacting the carrier with one functional group of a polyfunctional compound, followed by reacting another functional group of the polyfunctional compound with the enzyme.

One exemplary enzyme is papain, an enzyme obtained from unripe papaya. Papain linked to a polymer carrier is commercially available under the tradename Linked-Papain®. Linked-Papain® (papain carbomer, as described in CTFA, the International Cosmetic Ingredients Dictionary) is the enzyme papain in which papain is covalently linked to polyacrylic acid (900,000 daltons). Linked-Papain® is commercially available from Collaborative Laboratories, 3 Technology Drive, East Setauket, N.Y. 11733).

Once formed, the linked enzyme can be applied to the substrate to be treated by any known technique, including coating, such as brush coating, dipping, spraying, printing or any other known solution application process. In addition, the linked enzyme may be added to a polymer melt of a polymer precursor of a substrate to be formed. This would result in the linked enzyme being an internal additive. When the linked enzyme is added to the polymer melt of the precursor of the substrate, care must be taken so that the polymer processing conditions are not so extreme that the activity of the enzyme is adversely affected. Of these described methods, it is desirable to use a method in which less drying of the treated substrate is necessary. This will reduce the cost associated with drying treated substrates and the potential adverse effects that drying may have on the activity of the enzyme and the substrate which is treated with the linked enzyme. For cost and other reasons, it is usually desired to use the minimum amount of treatment composition that will produce the desired effect with an acceptable degree of uniformity. It is known, for example, that the heat of an additional drying step to remove water applied with the treatment composition can deleteriously affect strength properties of nonwovens as well as add cost to the process. It is desired to provide an improved treatment process and/or composition for nonwovens or other substrates that can efficiently and effectively apply the desired treatment without adversely affecting desirable nonwoven web or other substrate properties while also achieving the desired results.

The linked enzyme may be applied to the substrate to be treated in an amount from about 0.01% by weight to about 100% by weight based on weight of the substrate being treated. Desirably, the linked enzyme may be applied to the substrate to be treated in an amount from about 0.1 to about 25% based on the weight of the substrate being treated. More desirably, the linked enzyme may be applied to the substrate to be treated in an amount from about 5.0 to about 15% based on the weight of the substrate being treated. Most desirably, the linked enzyme may be applied to the substrate to be treated in an amount from about 8.0 to about 11% based on the weight of the substrate being treated. The amount of the linked enzyme can be varied so long as there is sufficient active enzyme present in the linked enzyme. Stated another way, at lower activity levels of the enzyme linked to the polymer, larger amounts of the linked enzyme may be necessary to achieve the desired result. At higher activity levels, lower amounts of the enzyme may be needed. As is also known in the art, activity is defined in terms of units. One unit (U) is defined as that amount which will catalyze the transformation of one micromole of substrate per minute under defined conditions. A unit can be seen as a measure of speed. The more units, the faster a particular reaction will occur. Industrial enzymes, both liquids and solids, are sold on a weight basis. Each kilogram is sold with a guaranteed activity. As the activity of an enzyme varies with temperature and pH among other factors, the test conditions have to be precisely defined. It is not enough to check the activity units of an enzyme. The process conditions affect the activity. Depending on the process conditions, more activity can be obtained from a given enzyme product. Thus, the manufacturer of enzymes must be consulted for the correct test procedure and unit measure. Units of activity usually cannot be compared directly with the units of activity from another manufacturer.

Generally, spraying or brushing the linked enzyme onto the substrate being treated may be employed, since these processes tend to reduce the need to dry the substrate treated with the linked enzyme. Typically, the composition used to spray or brush the linked enzyme onto the substrate contains the linked enzyme and a solvent. Solvents should be selected such that they do not adversely affect the activity of the enzyme. One suitable solvent is water.

Alternatively, the linked enzyme may be incorporated in an adhesive material which is used to bond the layers of the absorbent article together.

The substrates treated with the linked enzyme in accordance with the present invention can be used as a component of absorbent articles, including disposable personal care articles. When the linked enzyme treated substrate is used in an absorbent article, the treated substrate should be used in a layer which comes into contact with the fluid to be absorbed or another absorbent layer. A wide variety of disposable personal care absorbent articles for collecting bodily fluids, which articles typically contain nonwoven web materials, are known in the art. Disposable products of this type include some functional elements for receiving, distributing, absorbing, and retaining fluids. Typically, such absorbent articles have an absorbent core or other containment layer containing cellulosic fibers, for example, wood pulp fluff, particles of highly absorbent materials, for example, superabsorbents, and an admixture of cellulosic fibers and superabsorbents.

Given the ability of the linked enzyme treatment to cleave protein or carbohydrate-containing components of menses, such as mucin, the treated substrate makes for an excellent candidate for feminine care absorbent article such as tampons, pantiliners and feminine napkins.

An example of a personal care absorbent article is shown in FIG. 1, which shows the various layers generally present in a personal care absorbent article. FIG. 1 illustrates a representative personal care absorbent article product, in the form of a sanitary napkin structure. Other absorbent structures and configurations known to those skilled in the art may be used, including structures conventionally use for other absorbent articles, such as incontinence pads and garments, diapers, training pants and the like It is noted that other personal care absorbent articles have similar structures and the description of the present invention in terms of a sanitary napkin is not intended to limit the present invention. As shown, an absorbent article 30 includes baffle or backing layer 40, absorbent or containment layer 38, an optional distribution layer or intake layer 36, and body contacting layer or liner 34. If needed, the absorbent 38 may also be enclosed on its bottom and sides by wrap 32 for enhanced protection against side leakage. As shown, the absorbent layer is positioned between the backing layer or outer cover and the liner or body contacting layer. The optional distribution layer 36 is positioned between the absorbent layer 38 and the body contacting layer 34. In accordance with the invention, any or all of the cover, distribution or intake layers or absorbent layers may be treated with the linked enzyme, to enhance the ability of the absorbent article to absorb protein containing fluids.

The liquid impervious backing layer or outer cover (the baffle) 40 may include a layer constructed of any operative material, and may or may not have a selected level of liquid-permeability or liquid-impermeability, as desired. In a particular configuration, the backsheet or baffle 40 may be configured to provide an operatively liquid-impermeable baffle structure. The baffle may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Suitably, the baffle 28 can operatively permit a sufficient passage of air and moisture vapor out of the article, particularly out of an absorbent (e.g. storage or absorbent structure 30) while blocking the passage of bodily liquids. An example of a suitable baffle material can include a breathable, microporous film, such as those described in, for example U.S. Pat. No. 6,045,900 to McCormack et al.

Bicomponent films or other multi-component films can also be used, as well as woven and/or nonwoven fabrics which have been treated to render them operatively liquid-impermeable. Another suitable baffle material can include a closed cell polyolefin foam. For example, a closed cell polyethylene foam may be employed.

The liner or body contacting layer 34 is used to transport the fluid to be absorbed into the absorbent layers of the absorbent article. The liner or body side liner must be able to manage different body excretions depending on the type of product. In feminine care products, often the liner or body contacting layer must be able to handle menses and urine. In the present invention, the liner or body contacting layer 34 may include a layer constructed of any operative material, and may be a composite material. For example, the liner or body contacting layer can include a woven fabric, a nonwoven fabric, a polymer film, a film-nonwoven fabric laminate or the like, as well as combinations thereof. Examples of a nonwoven fabric include an airlaid fabric, spunbond fabric, meltblown fabric, coform fabric, a carded web, a bonded-carded-web, a bicomponent spunbond fabric, hydroentangled webs, spunlace webs or the like as well as combinations thereof. For example, the liner or body contacting layer can include a woven fabric, a nonwoven fabric, a polymeric film that has been configured to be operatively liquid-permeable, or the like, as well as combinations thereof. Other examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

Other examples of suitable materials are composite materials of a polymer and a nonwoven fabric material. The composite materials are typically in the form of integral sheets generally formed by the extrusion of a polymer onto a web of spunbond material. In a desired arrangement, the liner or body contacting layer 34 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the liner or body contacting layer. The apertures or other openings can help increase the rate at which bodily liquids can move through the thickness of the liner or body contacting layer and penetrate into the other components of the article (e.g. into the absorbent structure 30). The selected arrangement of liquid-permeability is desirably present at least on an operative portion of the liner or body contacting layer that is appointed for placement on the body-side of the article. The liner or body contacting layer 34 can provide comfort and conformability, and can function to direct bodily exudates away from the body and toward the absorbent structure 38. The liner or body contacting layer 34 can be configured to retain little or no liquid in its structure, and can be configured to provide a relatively comfortable and non-irritating surface next to the body-tissues of a female wearer. The liner or body contacting layer 34 can be constructed of any material which is also easily penetrated by bodily fluids that contact the surface of the cover layer.

The liner or body contacting layer 34 may be maintained in secured relation with the absorbent structure 38 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The liner or body contacting layer 34 typically extends over the upper, bodyside surface of the absorbent structure, but can alternatively extend around the article to partially or entirely, surround or enclose the absorbent structure 38. Alternatively, the cover 34 and the liquid impermeable layer 40 can have peripheral margins which extend outwardly beyond the terminal, peripheral edges of the absorbent structure 30, and the extending margins can be joined together to partially or entirely, surround or enclose the absorbent structure.

The distribution or intake layer 36 is sized and placed to more effectively operate in a target area of the absorbent layer 38 where liquids are more likely to be introduced into the article. The material of the intake layer can be configured to provide desired liquid-intake properties, substantially without consideration for delivering shaping properties. For example, the configuration of the intake layer need not include properties that are configured to prevent bunching and twisting of the article, particularly the absorbent structure, during ordinary wear.

The intake layer can include material that is configured to quickly absorb and pull liquid away from the body. Accordingly, the intake layer 36 can provide the function of liquid intake and can also provide the functions of liquid distribution, spreading, temporary storage and liquid retention. The intake layer may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof.

The absorbent structure 30 can be operatively configured to provide a desired level of absorbency or storage capacity. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural and/or synthetic fiber. Additionally, the absorbent body may include one or more components that can modify menses or intermenstrual liquid.

The absorbent structure 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g. saline with 0.9 wt % NaCl). The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc. The superabsorbent material may suitably be included in an appointed storage or retention portion of the absorbent system, and may optionally be employed in other components or portions of the absorbent article.

Other configurations of absorbent articles may also be utilized without departing form the scope of the present invention. For example, in the case of feminine care articles, feminine napkins, the absorbent article could have a configuration as described in, for example U.S. patent application Ser. No. 10/392,116, filed Mar. 19, 2003. It is noted that the absorbent articles described in this patent application may contain wings. It is possible to place the linked enzyme on the wing material, but little, if any, benefit will be obtained.

The linked enzyme of the present invention may be applied to any layer of the absorbent article which comes into contact with the viscoelastic fluid. Generally, the linked enzyme may be applied to any layer of the absorbent article from the body side layer to the absorbent layer and any layer which may be between the absorbent layer and the body side layer, since each of these layers comes into contact with the viscoelastic fluid. For example, the linked enzyme may be applied to the bodyside liner, the intake or distribution layer or the absorbent layer. Although the linked enzyme may be placed on the absorbent structure side of the outer layer baffle, little if any benefit may be obtained in placing the linked enzyme on the baffle. Desirably, the linked enzyme is placed on the intake or distribution layer or the body side layer. These layers are the first layer to come into contact with the viscoelastic fluid. However, this does not mean that the linked enzyme cannot be placed on other layers of the absorbent article, such as the absorbent layer. In addition, each layer of the absorbent article may be treated with the linked enzyme. In testing, when the linked enzyme is used, greater z-direction absorption is observed. In addition, as the loading of the linked enzyme increased, smaller stain sizes are obtained within the product.

In addition to the linked enzyme, other additives known in the art can be applied to the layers of the absorbent articles. These other additives may include other viscoelastant agents such as alkyl polyglycosides having 8-10 carbon atoms in the alkyl chain, which are described in U.S. Pat. No. 6,060,636 to Yahiaoui et al. These alky polyglycosides alter the viscoelastic properties of viscoelastic fluids as well as increase the wettability of synthetic surfaces. Other examples of viscoelastants include bovine lipid extract surfactant (Survanta, Ross Laboratories), a drug used to treat Acute Respiratory Distress Syndrome and Cystic Fibrosis. Some dextrans and dextran derivative, such as dextran sulfate, may also be used as viscoelastants. Dextrans are polymers of glucose with chain-like structures and molecular weights up to, for example, 2,000,000 daltons produced from sucrose, often by bacterial action. An exemplary dextran is a 4000 MW dextran available from Polydex Pharmaceuticals, Ltd. Of Scarborough, Canada. Other additives include conventional surfactants which have been used in absorbent articles, such as, for example ethoxylated hydrocarbons, siloxanes, and ionic surfactants have been shown to aid wicking. These additives may be present in the same layer as the linked-enzyme or may be present in layers in which the linked enzyme is not present. If these additives may be present on the same layer as the linked enzyme or in an adjacent layer, care should be taken to ensure that the linked enzymes activity is not adversely affected by additional additives.

Other additives including treatment chemistries such as cross-linking gelling agents, thickening agents, agglutinizing agents, plasma precipitators, mucolytic agents, lysing agents, odor absorbing agents and combinations thereof may also be used. The additional additives may be treated on the same layer of an absorbent article in which the linked enzyme is placed or on at least one of at least a portion of a surface of or interstices of another layer which comes into contact with the viscoelastic fluid.

It has been discovered that the use of the linked enzyme to treat at least one of the body side layer, the intake layer or the absorbent structure within a feminine sanitary napkin or liner, will reduce the amount of menses appearing on the surface of the napkin or liner. This indicates that the linked enzyme is able to improve the intake capabilities of these products. It was further discovered the when the linked-enzyme was used in conjunction with dextran, reduced fluid appearance on the body side layer of feminine care products is observed as compared to feminine care products in which a layer is only treated with a linked enzyme. Stated another way, the menses tends to spread less in the x and y directions within the layers when dextran is used in combination with the linked enzyme, while maintaining the z-direction absorption observed with the linked enzyme used by itself. However, the used of the linked enzyme alone reduces the degree of fluid appearance within the layers as compared to market products without the linked enzyme treatment.

The linked enzyme and any other viscoelastic treating agent may be uniformly dispersed through out an individual layer or substrate treated with the linked enzyme. Alternately, the linked enzyme and any other viscoelastic treating agent may be on the surface of the substrate or layer being treated, in a non-homogenous manner. Due to the cost considerations of the linked enzyme, it may be beneficial to treat less than the whole layer of the absorbent article. In this case, the center region of the layer, or the portion of the layer which comes into contact with the viscoelastic fluid should be the portion of the layer treated. Alternatively, the outer regions or areas surrounding the center region could be treated instead of the center region. When the outer regions are treated, leaks from the side could be prevented or reduced since the enzyme could act on the viscoelastic fluid as the viscoelastic fluid reaches the outer regions of the layer of the absorbent article. In addition, the treatment may be in zones or in a pattern on the individual layer or substrate treated with the linked enzyme.

Although described in terms of feminine care products, the linked enzyme may be used in other absorbent articles. For example, in adult care incontinence articles for absorbing cervical mucus and fecal fluids, in infant and child care products, such as diapers, in wound care products, such as bandages, in cleaning products, such a absorbent mops and wipes, especially for absorbing animal waste at veterinarian offices, zoos and the like, doctors offices, hospitals and operating rooms, grocery stores, restaurants, kitchens and the like.

The following Examples describe particular configurations of the invention, and are presented to provide a more detailed understanding of the invention. The Examples are not intended to limit the scope of the present invention in any way. From a complete consideration of the entire disclosure, other arrangements within the scope of the claims will be readily apparent to one skilled in the art.

EXAMPLES

In the following Examples 1 and 2, a menses simulant is used to test the effectiveness of the treatment of the present invention. In order to prepare the a menses simulant, blood, in this case defibrinated swine blood, is separated by centrifugation at 3000 rpm for 30 minutes, although other methods or speeds and times may be used if effective. The plasma is separated and stored separately, the buffy coat removed and discarded and the packed red blood cells stored separately as well. Eggs, in this case jumbo chicken eggs, are separated, the yolk and chalazae discarded and the egg white retained. The egg white is separated into thick and thin portions by straining the white through a 1000 micron nylon mesh for about 3 minutes, and the thinner portion discarded. Note that alternative mesh sizes may be used and the time or method may be varied provided the viscosity is at least that required. The material is then sheared by any appropriate method to achieve a homogeneous solution with a viscosity of about 20 cps at 150 sec$^{-1}$ at 22 degrees Celsius. After centrifuging, 80 mL of the thick homogenized egg white, which contains ovomucin, is added to a 300 cc FENWAL Transfer Pack using a syringe. Then, 60 cc of the swine plasma is added to the transfer pack. The transfer pack is clamped, all air bubbles removed, and placed in a Stomacher lab blender in which it is blended at normal (or medium) speed for about two minutes. The transfer pack is then removed from the blender, 60 cc of swine red blood cells are added, and the contents mixed by hand kneading for about two minutes, or until the contents appear homogeneous. The final mixture has a red blood cell content of about 30 volume percent and generally is at least within the range of 28-32 volume percent for artificial menses. The amount of egg white is about 40 weight percent. Simulants with higher or lower viscoelastic properties can be obtained by altering the ratio of homogenized thick egg white to blood plasma The ingredients and equipment used in the preparation of this artificial menses are readily available. Below is a listing of sources for the items used in the example, though of course other sources may be used providing they are approximately equivalent.

Blood (swine): Cocalico Biologicals, Inc., 449 Stevens Rd., Reamstown, Pa. 17567.

Fenwal® Transfer pack container, 300 ml, with coupler, sample 4R2014: Baxter Healthcare Corporation, Fenwal Division, Deerfield, Ill. 60015.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1194Z03127: Separation Technology, Inc., 1096 Rainer Drive, Altamont Springs, Fla. 32714.

Intake Test

The Intake Test determines differences between absorbent structures designed for absorption of menses simulant in the rate of intake. A 4 inch by 4 inch (10.16 cm by 10.16 cm) sample of the subject absorbent structure is used to perform the Intake Test.

For the purposes of this Intake Test, the menses is used. Established guidelines for handling blood-borne pathogens, including personal protection, handling and post-use sterilization must be followed when working with the swine blood based menses simulant. Prior to using the menses simulant for any procedure, the simulant is removed from the refrigerator and placed in a water bath for 10 minutes at 26° C. Before cutting open the bag for use, the bag is massaged between hands for a few minutes to mix the simulant, which will have separated in the bag. The bag tubing is then cut and the amount of simulant needed is poured out and stirred slowly to mix thoroughly before use.

Figure 2:
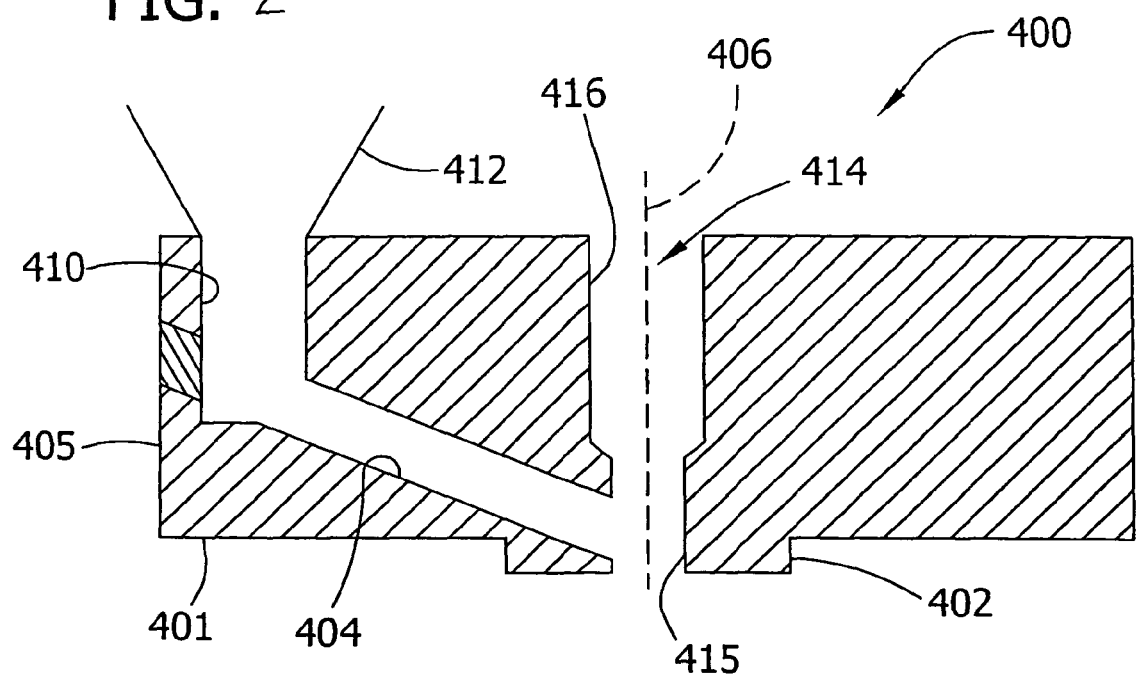
FIG. 2 is a vertical cross-section of a rate block for conducting an Intake Test on absorbent articles.
Figure 3:
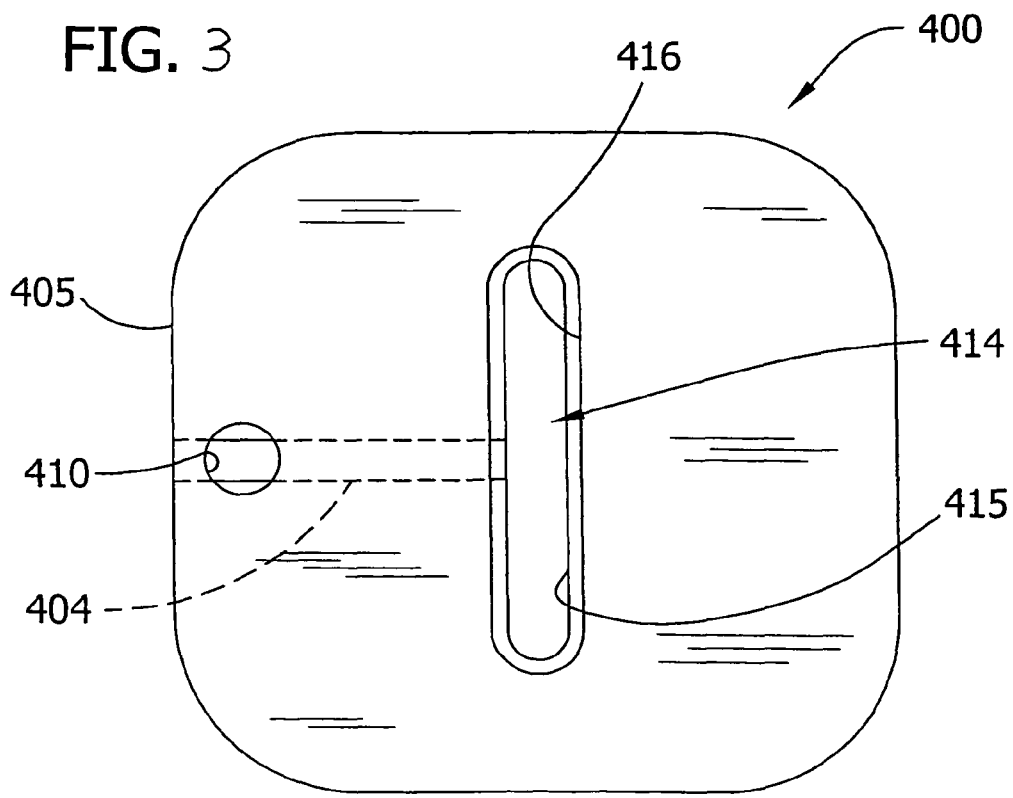
FIG. 3 is a plan view of the rate block of FIG. 2.

Referring to FIGS. 2 and 3, an acrylic rate block, generally indicated at 400, is 3 inches wide (76.2 mm) by 2.87 inches deep (72.9 mm) by 1.25 inches in height (31.8 mm). The rate block 400 includes a central portion 402 projecting out from the bottom 401 of the block, and a channel 404 extends diagonally downward from one side 405 of the rate block to a center line 406 thereof at an angle of about 22 degrees from horizontal. The channel 404 may be made by drilling the appropriately sized hole from the side 405 of the rate block 400 at the proper angle at a point above the bottom of the rate block; provided, however, that the starting point of the drill hole in the side 405 must be subsequently plugged so that menses simulant will not escape therefrom. A top hole 410 intersects the channel 404 and is on the side 405 and sized for receiving a funnel 412 therein. A central opening 414, a ¼ inch wide by 1¾ inches long slot, allows viewing of the progression of the menses simulant as it is taken into the absorbent structure. The central slot 414 is centered widthwise on the rate block 400 and has a bottom hole outlet 415 that is smaller in size than at the top 416 of the rate block. The top hole 410 and central slot 414 may also be formed in the rate block 400 in any suitable manner. The rate block is sized to have a predetermined weight and thus exert a preselected pressure/area (i.e. a weight of 161.9 grams will exert a pressure of 0.62 kPa over an area of 25.6 cm$^2$.

The rate block 400 is aligned with the long direction of the central opening 414 aligned with what would be the longitudinal direction of the absorbent structure material. The rate block 400 is then placed in the center of the sample to be tested and the sample is insulted with 2.0±0.01 ml of the menses simulant poured into the funnel 412. A stopwatch is started when the first insult reaches the test material. Once the simulant is taken completely into the sample, the stopwatch is stopped and the time on the stopwatch is recorded (e.g., in seconds) as the intake time of the first insult. The stopwatch is then reset. A timer is also started when the stopwatch is stopped and, after ten minutes have elapsed on the timer, a second insult of 2.0±0.01 ml of menses simulant is applied to the sample. The stopwatch is started to track the time needed for the sample to take in the second insult and the time is recorded as the second intake time. This procedure is repeated for the third insult also.

The Intake Test is conducted on five absorbent structure samples and the results are averaged to obtain the intake time and rewet data for a particular absorbent structure.

Example 1

A rheological test was used to demonstrate the performance of the composition of the invention. The testing was carried out using a Vilastic III capillary rheometer equipped with a 1 millimeter diameter capillary tube, available from Vilastic Scientific, P.O. Box 160261, Austin, Tex. 78716. The instrument was set up to take 10 time course measurements of a fluid's viscoelasticity in logarithmic increments. These measurements were taken at a single frequency of 0.5 Hz and shear rate of 1 to 10 s$^{-1}$. The directions provided with the rheometer were followed.

In this example, a linked enzyme is placed directly into the menses simulant. To use the simulant, the simulant is first warmed for 10 minutes at 22° C. in a water bath. The simulant is then manually mixed while in the transfer pack for about 4 minutes and until no visual separation is seen. The amount needed for testing is placed in a beaker and stirred at the lowest setting for 1 minute.

The results are shown in Table 1.

TABLE 1

| Share Rate s$^{-1}$ | Control Viscosity cP | Control Elasticity cP | 1% Linked Papain Viscosity Cp | 1% Linked Papain Elasticity Cp |
| --- | --- | --- | --- | --- |
| 1.091 | 18.50 | 6.38703 | 4.2514 | 4.272309 |
| 1.838 | 16.95 | 5.121446 | 4.225276 | 3.277367 |
| 3.089 | 15.66 | 3.494786 | 4.965787 | 0.996439 |
| 5.169 | 14.84 | 3.345144 | 4.497715 | 1.037968 |
| 8.657 | 14.24 | 3.077673 | 4.272175 | 0.952745 |

Example 2

In this example, the intake time of the simulant is measured. As in Example 1, the simulant is warmed using the procedure of Example 1 before use. A nonwoven web prepared by an air laying process containing 85% pulp and 15% binder fibers, was formed. The nonwoven web had a density of 0.6 g/cc and a basis weight of 175 gsm, and was cut into 4 inch by 4 inch samples. The control was untreated and the sample within the present invention were sprayed evenly across the surface of the sample with a solution containing water and papain linked to polyacrylic acid available as LINKED PAPAIN® from Collaborative Laboratories, and allowed to air dry for a period of time. Each sample within the present invention had about a 10% by weight of linked papain add-on. The intake rate for both the treated and untreated sample was measured using the intake test method described above. First, second and third insults were used in this example. The time needed for each insult to be absorbed by the nonwoven web was measured. The intake time and reduction results are shown in Table 2.

TABLE 2

| Insult | Control (no surface treatment)(Seconds to absorb) | 10% by weight papain linked to polyacrylic acid (seconds to absorb) | Percent Reduction in time |
| --- | --- | --- | --- |
| 1$^{st}$ gush | 15 | 11 | 27 |
| 2$^{nd}$ gush | 32 | 11 | 66 |
| 3$^{rd}$ gush | 65 | 22 | 66 |

As can be seen in Table 2, the linked enzyme reduces the time it take to absorb the menses simulant. In particular, the time it takes to absorb a second and third insult is nearly one-third of the time necessary for the control.

While the embodiments of the invention described herein are presently preferred, various modifications and improvements can be made without departing from the spirit and scope of the invention. The scope of the invention is indicated in the appended claims, and all changes that fall within the meaning and range of equivalents are intended to be embraced therein.

We claim:

1. An absorbent personal care article comprising a baffle layer, an absorbent layer and a body side liner layer, wherein the absorbent layer is positioned between the baffle layer and the body side liner layer, and at least one of the absorbent layer or the body side liner layer comprises a treating agent applied thereto, wherein the treating agent comprises a linked enzyme, said linked enzyme comprises an enzyme chemically linked to a carrier material and said carrier material comprises a material which is soluble or dispersible in a solution.

2. The absorbent personal care article according to claim 1, wherein the body side liner comprises the linked enzyme.

3. The absorbent personal care article according to claim 1, wherein the absorbent layer comprises the linked enzyme.

4. An absorbent personal care article comprising a baffle layer, an absorbent layer, an intake layer and a body side liner layer, wherein the absorbent layer is positioned between the baffle layer and the intake layer, the intake layer is positioned between absorbent layer and the body side liner layer, and at least one of the absorbent layer, the intake layer or the body side liner layer comprises a treating agent applied thereto, wherein the treating agent comprises a linked enzyme, said linked enzyme comprises an enzyme chemically linked to a carrier material and said carrier material comprises a material which is soluble or dispersible in a solution.

5. The absorbent personal care article according to claim 4, wherein the intake layer comprises the linked enzyme.

6. The absorbent personal care article according to claim 5, wherein the intake layer comprises a porous material selected from a film, a woven web, a knitted web, a foam or a nonwoven web.

7. The absorbent personal care article according to claim 6, wherein the intake layer comprises a nonwoven web selected from an airlaid nonwoven web, a meltblown nonwoven web, a spunbond nonwoven web or a coform nonwoven web.

8. The absorbent personal care article according to claim 7, wherein the nonwoven web comprises an air-laid nonwoven web and the nonwoven web comprises multicomponent fibers.

9. The absorbent personal care article according to claim 1, wherein the enzyme comprises a protease.

10. The absorbent personal care article according to claim 9, wherein the carrier material comprises a water soluble polymer selected from the group consisting polyvinylpyrolidone, polyacrylic acid, polyvinyl alcohol, polyalkylene oxide, a polyethylene glycol grafted polyvinylchloride or block or graft copolymers thereof.

11. The absorbent personal care article according to claim 10, wherein the protease comprises papain, bromelain, or mixtures thereof.

12. The absorbent personal care article according to claim 11, wherein the absorbent layer comprises a superabsorbent.

13. The absorbent personal care article according to claim 11, wherein the absorbent layer comprises pulp.

14. The absorbent article according to claim 1, wherein the enzyme comprises a protease, glycosidase or mixtures thereof.

15. The absorbent article according to claim 14, wherein the carrier material comprises a water soluble polymer selected from the group consisting of polyvinylpyrolidone, polyacrylic acid, polyvinyl alcohol, polyalkylene oxide, a polyethylene glycol grafted polyvinylchloride or block or graft copolymers thereof.

16. The absorbent personal care article of claim 1, wherein the treating agent is applied in a pattern on the absorbent layer or the body side liner layer.

17. The absorbent personal care article according to claim 1, wherein the treating agent is applied to the absorbent layer or the body side liner layer in an area of the layer which is most likely to come into contact with a viscoelastic fluid.

18. The absorbent personal care article according to claim 1, wherein the treating agent is uniformly dispersed on at least a portion of at least one of a surface and/or an interior of the absorbent layer or the body side liner layer.

19. The absorbent personal care article according to claim 1, wherein treating agent is dispersed on less than all of said layers of the absorbent personal care article.

20. The absorbent personal care article according to claim 1, wherein the treating agent is dispersed non-homogeneously within the absorbent layer or the body side liner layer.

21. The absorbent personal care article according to claim 1, wherein said treating agent is disposed in a center region of said absorbent layer.

22. The absorbent personal care article according to claim 1, wherein said treating agent is disposed in a center region of said body side liner layer.

23. The absorbent personal care article according to claim 4, wherein said treating agent is disposed in a center region of said intake layer.

24. A treated substrate comprising a substrate and a treating agent wherein the treating agent treats the substrate and the treating agent comprises a linked enzyme, wherein said linked enzyme comprises an enzyme chemically linked to a carrier material and said carrier material comprises a material which is soluble or dispersible in a solution, and wherein the substrate comprises a film, a woven web, a knitted web, or a nonwoven web.

25. The treated substrate according to claim 24, wherein the substrate comprises a nonwoven web.

26. The treated substrate according to claim 24, wherein the linked enzyme comprises a linked protease, glycosidase or mixtures thereof.

27. The treated substrate according to claim 24, wherein carrier material comprises a polymer.

28. The treated substrate according to claim 27, wherein the polymer comprises a water soluble polymer.

29. The treated substrate according to claim 28, wherein the polymer comprises polyvinylpyrolidone, polyacrylic acid, polyvinyl alcohol, polyalkylene oxide, a polyethylene glycol grafted polyvinylchloride or block or graft copolymers thereof.

30. The treated substrate according to claim 24, wherein the substrate comprises an absorbent material.

31. The treated substrate according to claim 30, wherein the absorbent material comprises pulp, a superabsorbent material or mixtures thereof.

32. The treated substrate according to claim 24, further comprising at least one second treating agent comprising cross-linking gelling agents, thickening agents, agglutinizing agents, plasma precipitators, mucolytic agents, lysing agents or combinations thereof.

33. The treated substrate according to claim 24, wherein the linked enzyme is present in an amount of 0.01 to about 100% by weight based on the weight of the substrate before treatment.

34. The treated substrate according to claim 33, wherein the linked enzyme is present in an amount of 0.1 to about 25% by weight based on the weight of the substrate before treatment.

35. The treated substrate according to claim 24, wherein the linked enzyme comprises papain linked to a polyacrylic acid, and the substrate comprises a nonwoven web.

36. The absorbent personal care article according to claim 1, further comprising at least one second treating agent comprising cross-linking gelling agents, thickening agents, agglutinizing agents, plasma precipitators, mucolytic agents, lysing agents or combinations thereof.

37. The absorbent personal care article according to claim 1, wherein the linked enzyme comprises papain linked to a polyacrylic acid and the linked enzyme is present in an amount of 0.1 to about 25% by weight based on the weight of the absorbent layer or the body side liner layer before treatment.

38. The absorbent personal care product according to claim 1, wherein the carrier material comprises a material which is soluble or dispersible in an aqueous solution.

* * * * *